(12) United States Patent
Vayron et al.

(10) Patent No.: US 7,462,632 B2
(45) Date of Patent: Dec. 9, 2008

(54) METHOD FOR THE PREPARATION OF N-PIPERIDINO-1, 5-DIPHENYLPYRAZOLE-3-CARBOXAMIDE DERIVATIVES

(75) Inventors: Philippe Vayron, Chateauneuf de Charbre (FR); Marc Daumas, Oraison (FR); Raphael Sole, Comps (FR); Alain Dlubala, Les Angles (FR)

(73) Assignee: Sanofi-Aventis, Paris (FR)

( * ) Notice: Subject to any disclaimer, the term of this patent is extended or adjusted under 35 U.S.C. 154(b) by 261 days.

(21) Appl. No.: 11/559,566

(22) Filed: Nov. 14, 2006

(65) Prior Publication Data

US 2008/0119653 A1     May 22, 2008

Related U.S. Application Data

(63) Continuation of application No. PCT/FR2005/001850, filed on Jul. 20, 2005.

(30) Foreign Application Priority Data

Jul. 22, 2004   (FR) .................................... 04 08111

(51) Int. Cl.
  *A61K 31/454* (2006.01)
  *C07D 401/00* (2006.01)
(52) U.S. Cl. ...................... 514/326; 546/211
(58) Field of Classification Search ................. 546/211; 514/326
See application file for complete search history.

(56) References Cited

U.S. PATENT DOCUMENTS 5,462,960 A * 10/1995 Barth et al. .................. 514/406

FOREIGN PATENT DOCUMENTS

EP        0656354        6/1997

* cited by examiner

*Primary Examiner*—Rita J Desai
*Assistant Examiner*—John Mabry
(74) *Attorney, Agent, or Firm*—Balaram Gupta

(57) ABSTRACT

A process for the preparation of for the preparation of N-piperidino-5-(4-chlorophenyl)-1-(2,4-dichlorophenyl)-4-methylpyrazole-3-carboxamide and of its salts, wherein 1,5-dibromopentane is reacted with a compound of formula (IIIa)

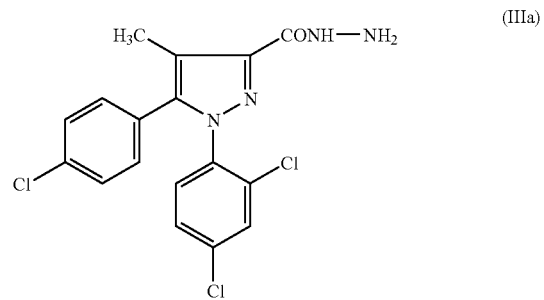

in the presence of $Na_2CO_3$ in acetonitrile heated at reflux.

11 Claims, No Drawings

US 7,462,632 B2

METHOD FOR THE PREPARATION OF N-PIPERIDINO-1,5-DIPHENYLPYRAZOLE-3-CARBOXAMIDE DERIVATIVES

CROSS-REFERENCE TO RELATED APPLICATIONS

This application is a continuation of International Application No. PCT/FR2005/001850 filed on Jul. 20, 2005 which is incorporated herein by reference in its' entirety which also claims the benefit of priority of French Patent Application No. 04/08111 filed on Jul. 22, 2004.

FIELD OF THE INVENTION

A subject matter of the present invention is a process for the preparation preparation of a compound of formula:

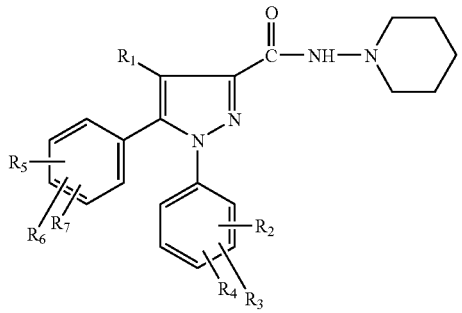

in which:
  $R_1$ represents a hydrogen or halogen atom or a ($C_1$-$C_4$) alkyl group;
  $R_2$, $R_3$, $R_4$, $R_5$, $R_6$ and $R_7$ each independently represent, a hydrogen or halogen atom or a ($C_1$-$C_4$)alkyl, ($C_1$-$C_4$) alkoxy or trifluoromethyl group;
  and their salts.

The compounds of formula (I) are disclosed in various patents or patent applications, for example, in EP 0 656 354 B and EP 1 150 961 B, they are disclosed as being as cannabinoid $CB_1$ receptor antagonists. More particularly, N-piperidino-5-(4-chlorophenyl)-1-(2,4-dichlorophenyl)-4-methylpyrazole-3-carboxamide generically known as rimonabant is the first medicine in a new class that targets multiple cardiometabolic risk factors, such as obesity and smoking

BACKGROUND OF THE INVENTION

Cardiometabolic risk may develop from a cluster of factors that can lead people to develop cardiovascular disease and/or type 2 diabetes. Main risk factors are abdominal obesity, high triglycerides (bad cholesterol), low HDL cholesterol level (good cholesterol), insulin resistance, elevated glucose and high blood pressure. The compounds produced by the process of the present invention are useful in the treatment of these conditions as adjuvants to diet and exercise and/or any other medically recognized therapeutic scheme for the treatment of obese or overweight patients with associated risk factors such as type-2 diabetes or dyslipidemia.

From a review of the relevant prior art, it is known that a compound of formula (I) can be prepared by the action of N-aminopiperidine on a functional derivative of the acid:

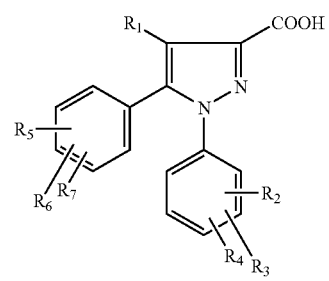

This synthetic process is disclosed in particular in patent EP 0 656 354 B for the preparation of rimonabant. A method for the treatment of patients with cardiometabolic risk factors such as obesity and smoking cessation is disclosed therein utilizing a functional derivative of the compound, for example, the alkyl ester or the acid chloride. This disclosure is also hereby incorporated by reference.

SUMMARY OF THE INVENTION

The present invention comprises a process for the preparation of N-piperidino-5-(4-chlorophenyl)-1-(2,4-dichlorophenyl)-4-methylpyrazole-3-carboxamide and of its salts, wherein 1,5-dibromopentane is reacted with a compound of formula (IIIa)

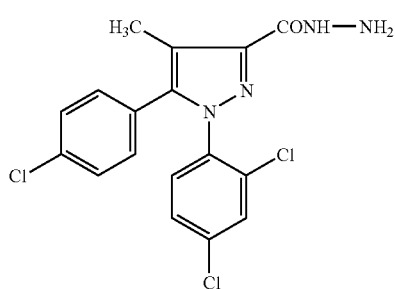

in the presence of $Na_2CO_3$ in acetonitrile heated at reflux.

DETAILED DESCRIPTION OF THE INVENTION

The subject matter of the present invention is a process for the preparation of a compound of formula:

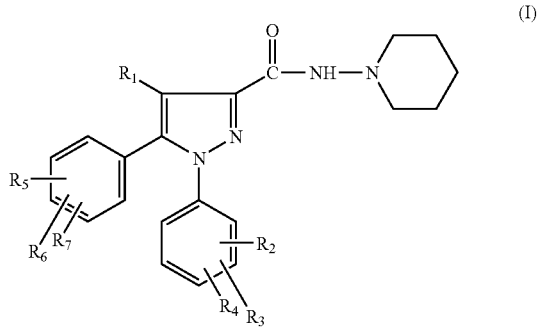

in which:

R₁ represents a hydrogen or halogen atom or a (C₁-C₄) alkyl group;

R₂, R₃, R₄, R₅, R₆ and R₇ each independently represent, a hydrogen or halogen atom or a (C₁-C₄)alkyl, (C₁-C₄) alkoxy or trifluoromethyl group;

and their salts. and of its salts, characterized in that:

a pentane derivative of formula:

X—(CH₂)₅—X'    (II)

in which X and X' each independently represent a halogen atom or a YSO₂O— group in which Y represents a (C₁-C₄) alkyl group, a (C₁-C₄)perfluoroalkyl group, an unsubstituted phenyl group or a phenyl group substituted by a methyl, chloro or nitro group, is reacted with a pyrazole-3-carbohydrazide derivative of formula:

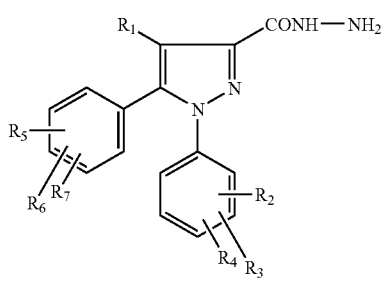
(III)

in which R₁, R₂, R₃, R₄, R₅, R₆ and R₇ are as defined above for (I), in the presence of a base, in a solvent and at a temperature between ambient temperature and the reflux temperature of the solvent.

According to the present invention, a compound of formula (I) is prepared by a process, wherein a pentane derivative of formula II X—(CH₂)₅—X' in which X and X' each independently represent a halogen atom or a YSO₂O— group in which Y represents a (C₁-C₄)alkyl group, a (C₁-C₄)perfluoroalkyl group, an unsubstituted phenyl group or a phenyl group substituted by a methyl, chloro or nitro group, is reacted with a pyrazole-3-carbohydrazide derivative of formula:

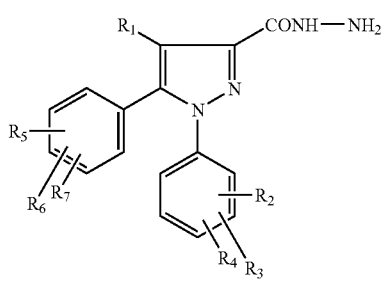
(III)

in which R₁, R₂, R₃, R₄, R₅, R₆ and R₇ are as defined above for formula(I).

The reaction is carried out in the presence of a base, in a solvent and at a temperature between ambient temperature and the reflux temperature of the solvent.

Preferably, the process of the invention is carried out utilizing a compound of formula (II) in which X and X' each independently represent a halogen atom.

More preferably, the process of the present invention utilizes a compound of formula (II) in which X and X' each independently represent a YSO₂O— group in which Y is as defined above.

A particularly preferred embodiment of the present invention comprises compounds of formula (II) in which 5-(4-chlorophenyl)-1-(2,4-dichlorophenyl)-4-methyl-1H-pyrazole-3-carbohydrazide of formula IIIa

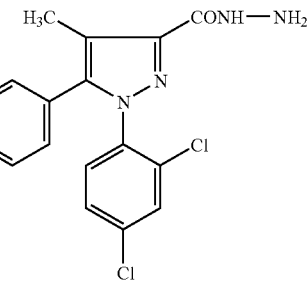
(IIIa)

More particularly, 1,5-dibromopentane is reacted with 5-(4-chlorophenyl)-1-(2,4-dichlorophenyl)-4-methyl-1H-pyrazole-3-carbohydrazide (IIIa).

The reaction is carried out in the presence of an organic base, such as a tertiary amine, for example triethylamine, or of an inorganic base, such as NaOH, KOH, K₂CO₃, Na₂CO₃ or CS₂CO₃.

The reaction may also be carried out in an aromatic solvent, for example toluene or chlorobenzene, in an ethereal solvent, for example tetrahydrofuran, dimethoxyethane or dioxane, or in a nitrile solvent, such as acetonitrile or propionitrile.

Preferably, the reaction is carried out in acetonitrile in the presence of triethylamine or Na₂CO₃ or K₂CO₃.

More preferably, the reaction is carried out in acetonitrile heated at reflux in the presence of Na₂CO₃.

Even more preferably, the present invention is a process for the preparation of N-piperidino-5-(4-chlorophenyl)-1-(2,4-dichlorophenyl)-4-methylpyrazole-3-carboxamide and of its salts, comprising 1,5-dibromopentane which is reacted with a compound of formula (IIIa) in the presence of Na₂CO₃ in acetonitrile heated to reflux.

The term "halogen atom" is understood to mean a bromine, chlorine or iodine atom.

Compounds of formula (III) and their preparation are known in the prior art: Canadian J. Chem., 1963, 41(7), 1813-1818; J. Chem. Engineering Data, 1977, 22(1), 104-110; J. Med. Chem., 2002, 45, 2708-2719.

The publication of J. Med. Chem., 2002, describes in particular 5-(4-chlorophenyl)-1-(2,4-dichlorophenyl)-4-methyl-1H-pyrazole-3-carbohydrazide and its preparation from the corresponding acid chloride.

The following examples are provided to better describe the present invention and to more specifically define the intermediate compounds produced thereby and how to produce said intermediates. It is emphasized that these are for illustrative purposes only and should not be construed as limiting the spirit and scope of the invention as later defined by the claims that follow.

In these examples and in the description, the following abbreviations are used:

A) DCM: dichloromethane.
B) The mass spectra are measured in electrospray (ES) ionization mode.
c) The proton nuclear magnetic resonance ($^1$H NMR) spectra are recorded at 200 MHz or at 300 MHz in $d_6$-DMSO or in $CDCl_3$. The chemical shifts δ are expressed in parts per million (ppm).
D) The signals observed in NMR are expressed thus: s: singlet; bs: broad singlet; d: doublet; sd: split doublet; t: triplet; st: split triplet; q: quartet; bup: broad unresolved peak; mt: multiplet.

Preparation 1

5-(4-Chlorophenyl)-1-(2,4-dichlorophenyl)-4-methyl-1H-pyrazole-3-carbohydrazide 20 g of 5-(4-chlorophenyl)-1-(2,4-dichlorophenyl)-4-methylpyrazole-3-carbonyl chloride in 100 ml of ethanol are placed under nitrogen and the mixture is heated at reflux for 2 hours. It is allowed to return to a temperature of 20-25° C., then 50 g of hydrazine hydrate are added and the mixture is again heated at reflux for 3 and a half hours. The reaction medium is filtered while hot and then the ethanol is evaporated. The reaction medium is concentrated, then taken up in 150 ml of DCM and separated by settling. The aqueous phase is discarded, the organic phase is washed twice with 100 ml of water and then the DCM is evaporated. After drying under vacuum, 16.9 g of the expected compound are obtained.

ES$^+$: [M+Na]$^+$=417, 419, 421, 423
ES$^-$: [M–H]$^-$=393, 395, 397, 399
NMR (CDCl$_3$, $^1$H at 300 MHz): 2.35 ppm: s: 3H; 4.0 ppm: d: 2H; 7.04 ppm: m: 2H; 7.25 ppm: bm: 4H; 7.41 ppm: d: 1H; 8.04 ppm: m: 1H.

EXAMPLE 1

N-Piperidino-5-(4-chlorophenyl)-1-(2,4-dichlorophenyl)-4-methylpyrazole-3-carboxamide 10 g of the compound obtained in Preparation 1 and 5.3 g of sodium carbonate are placed under nitrogen in 100 ml of acetonitrile. The reaction medium is heated to reflux of the acetonitrile, a total of 6.9 ml of 1,5-dibromopentane is added and then heating is maintained at reflux over 45 hours. The medium is hydrolyzed by addition of 50 ml of water, separation by settling is allowed to take place and the aqueous phase is discarded. The organic phase is washed twice with 50 ml of a saturated aqueous NaCl solution. The acetonitrile is evaporated to dryness and 18.4 g of a crude product are obtained. The crude product obtained is chromatographed on silica gel (eluent cyclohexane/acetone: 75/25; v/v). The product obtained is taken up in 100 ml of methylcyclohexane and recrystallized. 5.7 g of the pure expected compound are obtained.

NMR (d$_6$-DMSO, $^1$H at 200 MHz): 1.31 ppm: bm: 2H; 1.55 ppm: bm: 4H; 2.22 ppm: s: 3H; 4.0 ppm: d: 2H; 7.22 ppm: d: 2H; 7.43 ppm: d: 2H; 7.56 ppm: sd: 1H; 7.71 ppm: d: 1H; 7.76 ppm: d: 1H; 9.02 ppm: s: 1H.

What is claimed is:

1. A process for the preparation of a compound of formula:

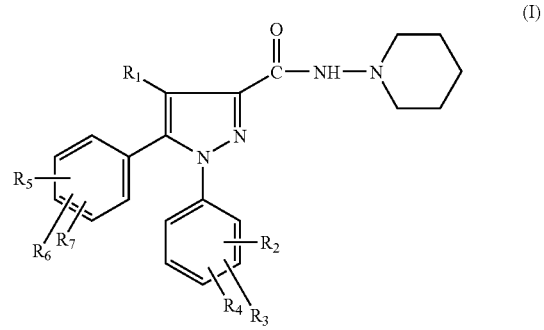

wherein:
$R_1$ represents a hydrogen or halogen atom or a ($C_1$-$C_4$) alkyl group;
$R_2$, $R_3$, $R_4$, $R_5$, $R_6$ and $R_7$ each independently represent, a hydrogen or halogen atom or a ($C_1$-$C_4$)alkyl, ($C_1$-$C_4$) alkoxy or trifluoromethyl group;
and of its salts, characterized in that:
a pentane derivative of formula:

in which X and X' each independently represent a halogen atom or a $YSO_2O$— group in which Y represents a ($C_1$-$C_4$)alkyl group, a ($C_1$-$C_4$)perfluoroalkyl group, an unsubstituted phenyl group or a phenyl group substituted by a methyl, chloro or nitro group, is reacted with a pyrazole-3-carbohydrazide derivative of formula:

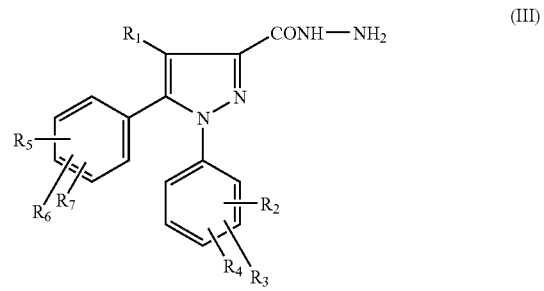

in which $R_1$, $R_2$, $R_3$, $R_4$, $R_5$, $R_6$ and $R_7$ are as defined above for (I), in the presence of a base, in a solvent and at a temperature between ambient temperature and the reflux temperature of the solvent.

2. The process as recited in claim 1, wherein in the compound of formula (II), X and X' each independently represent a halogen atom.

3. The process as recited in claim 1, wherein in the compound of formula (II), X and X' each independently represent a Y—SO$_2$—O— group in which Y is as defined in claim 1.

4. The process as recited in claim 3 for the preparation of N-piperidino-5-(4-chlorophenyl)-1-(2,4-dichlorophenyl)-4-methylpyrazole-3-carboxamide and of its salts, wherein;
a compound of formula (II) is reacted with 5-(4-chlorophenyl)-1-(2,4-dichlorophenyl)-4-methyl-1H-pyrazole-3-carbohydrazide of formula (IIIa):

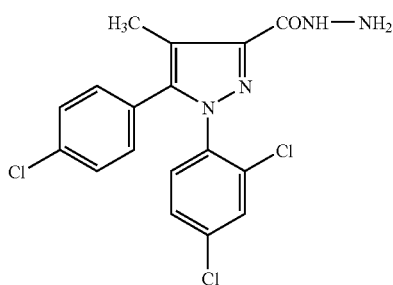

5. The process as recited in claim 4, wherein a 1,5-dihalopentane is reacted with the compound of formula (IIIa).

6. The process as recited in claim 5, wherein 1,5-dibromopentane is reacted with the compound of formula (IIIa).

7. The process as recited in claim 6, characterized in that the base is chosen from triethylamine, NaOH, KOH, $K_2CO_3$, $Na_2CO_3$ or $Cs_2CO_3$.

8. The process as recited in claim 7, characterized in that the solvent is chosen from toluene, chlorobenzene, tetrahydrofuran, dimethoxyethane, dioxane, acetonitrile or propionitrile.

9. The process as recited in claim 8, wherein the reaction is carried out in the presence of triethylamine, $Na_2CO_3$ or $K_2CO_3$ in acetonitrile.

10. The process as recited in claim 9, wherein the reaction is carried out in the presence of $Na_2CO_3$ in acetonitrile heated at reflux.

11. A process for the preparation of N-piperidino-5-(4-chlorophenyl)-1(2,4-dichlorophenyl)-4-methylpyrazole-3-carboxamide and of its salts, wherein 1,5-dibromopentane is reacted with a compound of formula (IIIa)

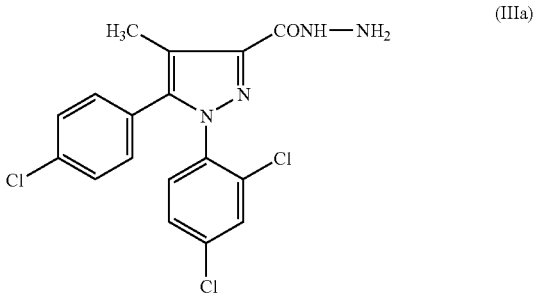

in the presence of $Na_2CO_3$ in acetonitrile heated at reflux.

* * * * *